_United States Patent_ [19]

Wilke et al.

[11] Patent Number: 4,968,610

[45] Date of Patent: Nov. 6, 1990

[54] PROCESS FOR THE PREPARATION OF CHANOCLAVINE

[75] Inventors: Detlef Wilke, Wennigsen/Deister; Alfred Weber, Berlin, both of Fed. Rep. of Germany

[73] Assignee: Schering Aktiengesellschaft, Berlin and Bergkamen, Fed. Rep. of Germany

[21] Appl. No.: 842,704

[22] PCT Filed: May 30, 1985

[86] PCT No.: PCT/DE85/00191

§ 371 Date: Feb. 3, 1986

§ 102(e) Date: Feb. 3, 1986

[87] PCT Pub. No.: WO85/05633

PCT Pub. Date: Dec. 19, 1985

[30] Foreign Application Priority Data

Jun. 1, 1984 [DE] Fed. Rep. of Germany ....... 3420954

[51] Int. Cl.$^5$ ...................... C12P 17/18; C12N 1/14

[52] U.S. Cl. .................................... 435/119; 435/254; 435/911

[58] Field of Search ............... 435/119, 911, 171, 118, 435/254

[56] References Cited

PUBLICATIONS

Tscherter et al., *Helvetica Chimica Acta* vol. 57, 1974, pp. 113–121.

Singh et al., *Indian J. Exp. Biol.* vol. 15, pp. 585–6; 1977.

Sanardhanan et al., *Foliamicrobiol.* vol. 27, pp. 121–125 (1982).

Floss, H, *Tetrahedron,* vol. 32, pp. 813–912, 1976.

*Primary Examiner*—Elizbeth C. Weimar
*Assistant Examiner*—Irene Marx
*Attorney, Agent, or Firm*—Millen, White & Zelano

[57] ABSTRACT

A process is claimed for the preparation of chanoclavine, characterized by cultivating the microorganism *Claviceps* spec. DSM 2837 and isolating the thus-formed chanoclavine after termination of fermentation.

2 Claims, No Drawings

PROCESS FOR THE PREPARATION OF CHANOCLAVINE

The invention relates to the process characterized in the claims.

Chanoclavine=2-methyl-3-[1,3,4,5-tetrahydro-4-(methylamino)benz[cd]indol-5-yl]-2-propen-1-ol represents, as is known, a precursor for the biosynthesis of pharmacologically active ergot alkaloids and can be utilized, inter alia, for the production of pharmacologically effective compounds. (J. Med. Chem., 17 : 300, 1974.)

It has been found that a fungal strain *Claviceps* spec. excretes chanoclavine in high yields and practically free of other ergot alkaloids into the culture medium. This strain, *Claviceps* spec., was isolated from an ergot of brome grasses (*Bromus*) growing in the wild. It has the internal name SCHERING, MBCE 373113 and has been placed in the German collection for microorganisms under number DSM 2837. The strain forms compact, greatly wrinkled colonies which are white and become reddish with age, on agar media with glucose or sucrose as the carbon source and asparagine, ammonium succinate or ammonium citrate as the nitrogen source, these colonies consisting of hyphae exhibiting vacuoles showing extensive light refraction with aging.

The hyphae have a diameter of 3–4 μm. There is no formation of conidia. The colony diameter is 3–4 cm after a cultivating period of 10 days, and 6–7 cm after a cultivating time of 20 days.

The process of this invention is performed under conditions usually employed for incubation of fungal cultures for metabolic synthesis. Thus, first a determination is made in generally customary preliminary tests to find the most favorable fermentation conditions, such as, for example, the choice of the most favorable nutrient medium, of the technical conditions, such as temperature, aeration, pH value, and of the optimum time periods for germination and for the development of the microorganism.

A suitable carbon source for the fermentation medium can be, for example, glucose or sucrose. Inter alia, asparagine, ammonium succinate or ammonium citrate are utilized to serve as the nitrogen source. The medium furthermore contains the required growth promoters (e.g. yeast extract) and mineral substances (potassium, magnesium, calcium, iron, and zinc cations, as well as sulfate, phosphate, and nitrate anions) in the usually employed concentration.

Fermentation can take place in one or two stages; in this connection, the medium employed for the subculture can be identical to that of the main culture or can be different therefrom. Germination and propagation take place preferably at a lower concentration of carbon source (10–100 g/l); chanoclavine production proper is preferably carried out at a higher concentration of carbon source (100–300 g), glucose being employed with preference a the carbon source.

At the beginning of fermentation, the pH of the medium is preferably set to be in a range from 4 to 6. The incubating temperature ranges from about 10° to 35° C., preferably from 20° to 30° C. The culturing conditions are strictly aerobic. The optimum fermentation period is determined in the usual way by analysis of the thus-formed chanoclavine.

After fermentation has taken place, the thus-formed chanoclavine is isolated conventionally, for example by extracting the fermentation batches with an organic solvent immiscible with water, such as ethyl acetate, methyl isobutyl ketone, dichloromethane, chloroform, or tetrachloroethane, concentration of the extracts, and purification of the resultant crude product by chromatography and/or crystallization.

The example set forth below serves for an explanation of the process of this invention.

EXAMPLE

*Claviceps* spec. DSM 2837 is grown on a nutrient medium containing the following ingredients:

Sucrose (100 g/l), citric acid (10 g/l), yeast extract (0.1 g/l), potassium hydrogen phosphate (500 mg/l), magnesium sulfate heptahydrate (300 mg/l), ammonium sulfate (69 mg/l), calcium nitrate tetrahydrate (1 g/ ), iron sulfate heptahydrate (7 mg/l), zinc sulfate heptahydrate (6 mg/l). The nutrient medium is adjusted to pH 5.1. The incubation culture is stored in an incubator at 30° C. for 14–28 days.

A piece of mycelium of a size of about 1 $cm^2$ is comminuted under sterile conditions by an "Ultra Turrax" mixer in 5 ml of physiological sodium chloride solution and used for inoculating 50 ml of a subculture containing glucose (50 g/l), citric acid (7.5 g/l), potassium dihydrogen phosphate (500 mg/l), magnesium sulfate heptahydrate (300 mg/l), ammonium nitrate (6 g/l), calcium nitrate tetrahydrate (1 g/l), zinc sulfate heptahydrate (6 mg/l), iron(II) sulfate heptahydrate (7 mg/l), yeast extract (100 mg/l)—adjusted to pH 5.1—provided in a 500 ml Erlenmeyer flask, and cultivated on a circular vibrator for 4 days at 24° C. and 220 rpm.

5 ml of the resultant subculture is transferred into 50 ml of a medium containing sucrose (200 g/l), citric acid (10 g/l), yeast extract (0.1 g/l), potassium dihydrogen phosphate (500 mg/l), magnesium sulfate heptahydrate (300 mg/l), ammonium sulfate (6 g/l), calcium nitrate tetrahydrate (1 g/l), iron sulfate heptahydrate (7 mg/l), and zinc sulfate heptahydrate (6 mg/l)—adjusted to pH 5.1—disposed in a 500 ml Erlenmeyer flask, and shaken on a circular vibrator for 9 days at 24° C. at 240 rpm.

The culture medium is then removed by filtration, and the content of chanoclavine is determined by photometry using the van Urk reaction (Mikrochim. Acta, 619–630, 1959). The concentration of the culture filtrate is 390 mg/l. No further ergot alkaloids can be detected by thin-layer chromatography.

We claim:

1. A process for the preparation of chanoclavine, characterized by cultivating the microorganism *Claviceps* spec. DSM 2837 and isolating the thus-formed chanoclavine after termination of fermentation.

2. A biologically pure culture of *Claviceps* spec., DSM 2837.

* * * * *